United States Patent [19]

Mino et al.

[11] Patent Number: 5,455,360

[45] Date of Patent: Oct. 3, 1995

[54] 1-PYRROLYL SILICON COMPOUNDS, CHEMICALLY ADSORBED ULTRATHIN FILM FORMED THEREFROM AND METHOD OF MANUFACTURING THE SAME

[75] Inventors: Norihisa Mino, Settsu; Kazufumi Ogawa, Nara; Ishihara Toshinobu, Joetsu; Mikio Endo, Joetsu; Tohru Kubota, Joetsu; Katsuya Takemura, Joetsu, all of Japan

[73] Assignee: Matsushita Electric Industrial Co., Ltd., Osaka, Japan

[21] Appl. No.: 107,886

[22] Filed: Aug. 18, 1993

[30] Foreign Application Priority Data

Sep. 10, 1992 [JP] Japan .................. 4-242351

[51] Int. Cl.$^6$ .................. C07F 7/10; C07D 207/323
[52] U.S. Cl. .................. 548/406
[58] Field of Search .................. 548/406

[56] References Cited

U.S. PATENT DOCUMENTS 3,346,588 10/1967 Ashby .................. 548/406
5,081,260 1/1992 Kubota et al. .................. 548/406

FOREIGN PATENT DOCUMENTS 392509 10/1990 European Pat. Off. .................. 548/406
0445534 9/1991 European Pat. Off. .

OTHER PUBLICATIONS

Journal of the American Chemical Society, vol. 105, 1983, pp. 5690–5691, T. Komori et al., "Electroorganic Reactions on Organic Electrodes. 3. Electrochemical Assymetric Oxidation of Phenyl Cyclohexyl Sulfide on". . .

J. Am. Chem. Soc. 104, 2031–2034, 1982, Synthesis and . . . pyrrole, Simon et al.

CA 96(16):131966z Synthesis . . . pyrrole. Simon et al., 1982.

CA 99(9):69833k Stereochemical . . . electrodes, Komori et al., 1983.

CA 101(2):13898c Electroorganic . . . electrodes, Komori et al., 1984.

CA 115(6):62592w Silicon–containing . . . therefrom, Nagasubramanian et al., 1991.

*Primary Examiner*—Joseph K. McKane
*Attorney, Agent, or Firm*—Fish & Richardson

[57] ABSTRACT

Disclosed are a conductive pyrrole derivative monomolecular film covalently bonded to a substrate surface and method of manufacturing the same, and a monomer used for forming the conductive pyrrole derivative monomolecular film and method of manufacturing the same. The invention relates to a monomolecular ultrathin film comprising 1-pyrrolyl groups and silicon groups. The monomer used for forming the film is provided by reacting ω-(1-pyrrolyl)-1-alkene compound to a monosilane derivative compound, in which three out of four hydrogen atoms of monosilane are replaced with halogen or alkoxy groups, in the presence of a transition metal catalyst. A substrate is dipped and held in a nonaqueous solution of the above-noted monomer, thus chemically bonding a monomolecular film to a substrate surface. Furthermore, a polypyrrole derivative ultrathin film is formed by the electrolytic or catalytic polymerization of the monomolecular film.

4 Claims, 3 Drawing Sheets

1-PYRROLYL SILICON COMPOUNDS, CHEMICALLY ADSORBED ULTRATHIN FILM FORMED THEREFROM AND METHOD OF MANUFACTURING THE SAME

FIELD OF THE INVENTION

This invention relates to a new material—a silicon compound comprising 1-pyrrolyl groups—and a method of manufacturing the same, and a chemically adsorbed ultrathin film comprising the compound and a method of manufacturing the same. This invention also relates to a silicon polypyrrole derivative ultrathin film and a method of manufacturing the same.

BACKGROUND OF THE INVENTION

Polypyrrole has been known as an organic conductive ultrathin film. A conductive polypyrrole can be formed by the electrolytic polymerization of a pyrrole derivative. This conductive polypyrrole has been applied to electronic devices such as diodes and field effect transistors, and to optoelectronic devices including electrochromic elements, optical memory elements and the like. Due to the recent miniaturization of devices, conductive films are consequently required to be made thinner. It has also been a goal to develop a pyrrole derivative which can form a conductive ultrathin film much more easily and consistently than other materials.

Forming a conductive ultrathin film on a substrate surface by using a pyrrole derivative can be done by the following procedure:

providing a monomer by bonding long-chain organic groups to pyrrole;

forming a monomer monomolecular film on a substrate surface by the Langmuir-Blodgett method (LB method); and polymerizing the film on the substrate surface.

However, in the case of this conventional pyrrole derivative, the monomolecular film is only physically adsorbed to the substrate even by the LB method. The monomer is also likely to be evaporated or scattered before or during the polymerization process. Therefore, it has been difficult to form a fully optimal conductive ultrathin film.

SUMMARY OF THE INVENTION

In order to solve the above-noted problems, the objectives of this invention are to provide a new silicon compound comprising 1-pyrrolyl groups—a pyrrole derivative which can easily and firmly form an adsorbed monomolecular film on a substrate surface—and a method of manufacturing the same; to form a chemically adsorbed ultrathin film comprising the silicon compound mentioned above and a method of manufacturing the same; and to form a polypyrrole derivative ultrathin film by using the chemically adsorbed ultra thin film and a method of manufacturing the same.

The chemically adsorbed ultrathin film of this invention is comprising 1-pyrrolyl groups and silicon groups of Formula 1:

Formula 1

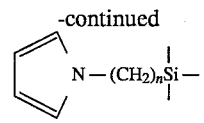

(wherein n represents an integer from 6 to 30).

The polypyrrole conductive ultrathin film of this invention is formed by the ring-opening polymerization of the pyrrolyl groups of the chemically adsorbed ultrathin film comprising 1-pyrrolyl groups and silicon groups.

The method of manufacturing the chemically adsorbed ultrathin film of this invention is a method of manufacturing a chemically adsorbed ultrathin film on a substrate surface having active hydrogen groups, which entails:

contacting a chemical compound of Formula 2 below to the active hydrogen groups on the substrate surface in a liquid—or gaseous-phase atmosphere, thus generating a dehydrochlorination or alcohol elimination reaction and forming a chemically adsorbed ultrathin film comprising 1-pyrrolyl groups and silicon groups on the substrate surface.

Formula 2

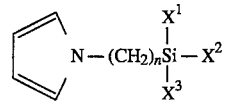

(wherein $X^1$, $X^2$ and $X^3$ can be the same or different and represent a halogen atom or an alkoxy group with 1–4 carbon atoms; n represents an integer from 6 to 30)

It is preferable in this invention that, after the formation of the above-noted chemically adsorbed ultrathin film, the film is dipped and held in an electrolytic solution to polymerize the film by electrolytic polymerization.

It is also preferable in this invention that, after the formation of the above-noted chemically adsorbed ultrathin film, the film is dipped and held in a catalytic solution to polymerize the film by catalytic polymerization.

The new chemical compound of this invention is a material used for manufacturing a chemically adsorbed ultrathin film comprising the 1-pyrrolyl groups and silicon groups of Formula 1, and is comprised of the 1-pyrrolyl groups and silicon groups of Formula 3:

Formula 3

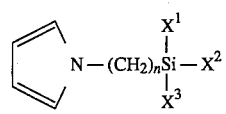

(wherein $X^1$, $X^2$ and $X^3$ are the same or different and represent a halogen atom or an alkoxy group with 1–4 carbon atoms; n represents an integer from 6 to 30).

The method of manufacturing the material used for manufacturing the chemically adsorbed ultrathin film comprising 1-pyrrolyl groups and silicon groups consists of adding and reacting the ω-(1-pyrrolyl)-1-alkene of Formula 4 with the silicon hydride of Formula 5 in the presence of a transition metal catalyst.

Formula 4

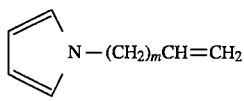

(wherein m represents an integer from 4 to 28)

FORMULA 5

HSiX$^1$X$^2$X$^3$ (wherein X$^1$, X$^2$ and X$^3$ are the same or different and represent a halogen atom or an alkoxy group with 1–4 carbon atoms)

The Si—X groups of the silicon compound comprising 1-pyrrolyl groups of this invention are reacted to hydroxy groups on the substrate surface. Alternatively, hydrolysis is generated due to the contact of the Si—X groups to the hydroxy groups. As a result, covalent bonds such as siloxane bonds are created at the substrate surface, and the compound is chemically adsorbed to the surface. Since the chemically adsorbed ultrathin film (monomolecular film) formed by the compound of this invention is firmly chemically bonded to the surface via covalent bonds, the film can keep its strength and uniform thickness without evaporating or scattering the compound. The thickness of the film can be at the angstrom or nanometer level.

A conductive ultrathin film formed by the electrolytic or catalytic polymerization of the above-noted chemically adsorbed ultrathin film (monomolecular film) can be applied to microelectronic devices or microoptoelectrinic devices.

DETAILED DESCRIPTION OF THE INVENTION

EXAMPLES

Figure 1:
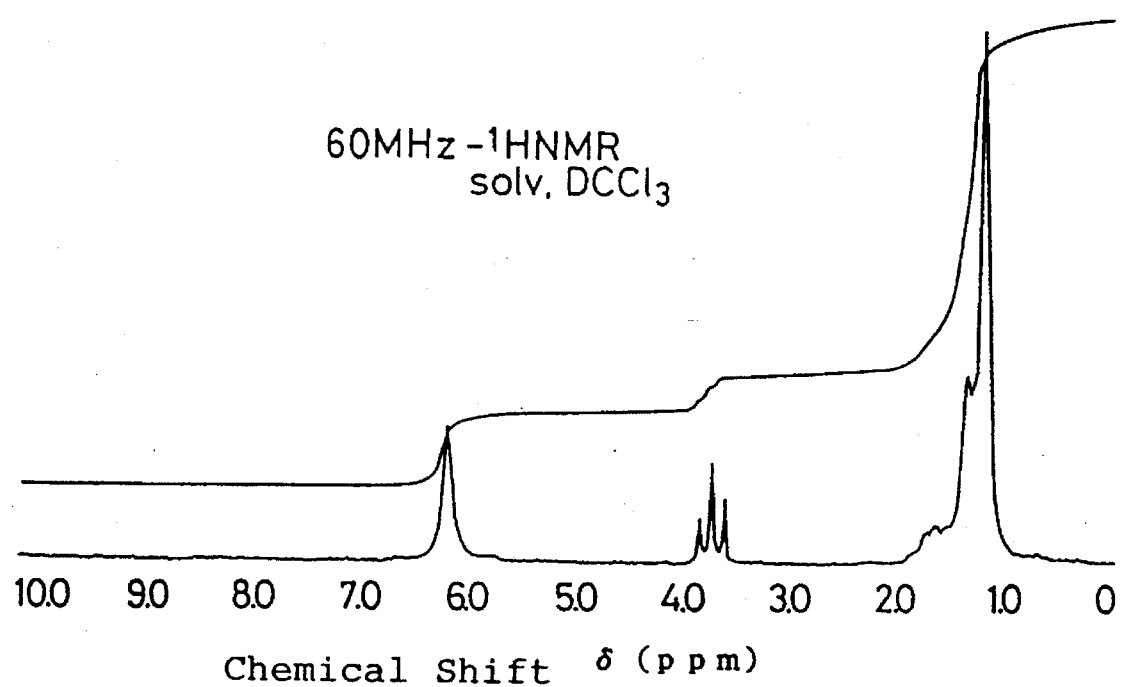
FIG. 1 is a graph showing the nuclear magnetic resonance spectrum of 10-(1-pyrrolyl)-decyltrichlorosilane of Example 1.

The invention is specifically described by referring to the following examples.

The examples of new chemical compounds of the invention are as follows:

ω-(1-pyrrolyl)-alkyl-trihalogenosilane;
Si-[ω-(1-pyrrolyl)-alkyl]-alkoxy-dihalogenosilane;
Si-[ω-(1-pyrrolyl)-alkyl]-dialkoxy-halogenosilane; and
Si-[ω-(1-pyrrolyl)-alkyl]-trialkoxysilane.

The alkyl groups of the examples are straight chains, comprising 6–30 carbon atoms. In forming a chemically adsorbed ultrathin film (monomolecular film) on a substrate surface, molecular chains are likely to become intertwined when there are more than 30 carbon atoms in a group. It is not preferable to have intertwined molecular chains, which prevent the formation of a film with the required precision. In a case that there are less than 6 carbon atoms in a group, the interaction among the carbon chains becomes small; as a result, a chemically adsorbed ultrathin film (monomolecular film) cannot be formed. The number of carbon atoms of the alkoxy groups is 1–4.

The halogen can be either chlorine or bromine.

More specifically, the chemical compounds which can be used in the invention are as follows:

Formula 6: ω-(1-pyrrolyl)-octyl-trichlorosilane

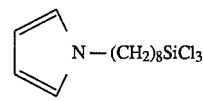

Formula 7: ω-(1-pyrrolyl)-decyl-trichlorosilane

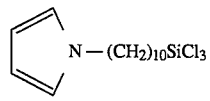

Formula 8: ω-(1-pyrrolyl)-tetradecyl-trichlorosilane

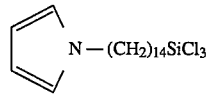

Formula 9: Si-(ω-(1-pyrrolyl)-decyl)-trimethoxysilane

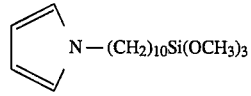

Formula 10: Si-(ω-(1-pyrrolyl)-tetradecyl)-trimethoxysilane

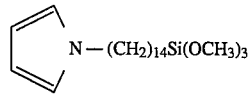

The chemical compounds of Formulas 6–10 above can be provided by reacting silicon hydride compounds with ω-(1-pyrrolyl)-1-alkene compounds.

As shown in the following Formulas 11–14, these ω-(1-pyrrolyl)-1-alkene compounds are compounds in which 1-pyrrolyl groups are bonded to the end of straight-chain 1-alkene comprising 6–30 carbon atoms. These compounds can be easily synthesized from pyrrole by the method of C. F. Hobbs (J. Am. Chem. Soc., 84, 43 (1962)) or the like.

Formula 11: ω-(1-pyrrolyl)-1-decene

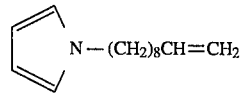

Formula 12: ω-(1-pyrrolyl)-1-dodecene

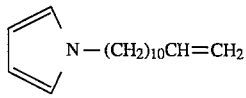

Formula 13: ω-(1-pyrrolyl)-1-hexadecene

-continued

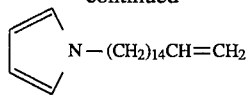

Formula 14: ω-(1-pyrrolyl)-1-docosene

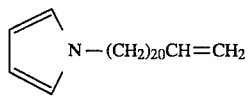

These silicon hydride compounds are monosilane derivative compounds in which three out of four hydrogen atoms of monosilane are replaced with halogen or alkoxy groups. The halogen is chlorine, bromine or the like. A methoxy group, an ethoxy group or the like is included as an alkoxy group.

The monosilane derivative compounds mentioned above can include the following:

trichlorosilane ($HSiCl_3$);

tribromosilane ($HSiBr_3$);

trimethoxysilane ($HSi(OCH_3)_3$);

triethoxysilane ($HSi(OCH_2CH_3)_3$); and dimethoxychlorosilane ($HSiCl(OCH_3)_2$).

In reacting the silicon hydride compounds with the above-mentioned ω-(1-pyrrolyl)-1-alkene compounds, transition metal catalysts are used.

More specifically, the transition metal catalysts mentioned above are as follows:

hydrogenhexachloroplatinate ($H_2PtCl_6$);

dichlorobis(triphenylphosphine)platinate(II) ($[PtCl_2(PPh_3)_2]$);

dichlorobis(triphenylphosphine)palladium(II) ($[PdCl_2(PPh_3)_2]$); and chlorotris(triphenylphosphine)rhodium(I) ($[RhCl(PPh_3)_3]$).

Either one or a mix of the transition metal catalysts can be used in the invention.

The quantity of the catalyst needed for the reaction is suitably 10–500 ppm relative to that of the ω-(1-pyrrolyl)-1-alkene compound.

A reactor equipped with an agitator, thermometer, reflux condenser and dropping funnel can be used for the reaction described above. The reaction temperature is 20°–150° C., and the silicon hydride compound is dropped from the funnel onto the ω-1-pyrrolyl) -1-alkene compound in the reactor. As reaction solvents, aprotic solvents including toluene, xylene, tetrahydrofuran (THF) or the like can be used.

Through a distillation procedure under reduced pressure after the reaction, a highly pure ω-(1-pyrrolyl)-alkylsilane compound is generated. The obtained compound can be observed by mass spectrum, nuclear magnetic resonance spectrum, infrared absorption spectrum or like techniques.

A chemically adsorbed ultrathin film (monomolecular film) is formed on a substrate surface by using the above-noted silicon compound comprising 1-pyrrolyl groups (chemical adsorbent) by the following procedure:

preparing a substrate which has—or is given—active hydrogens such as hydroxyl groups (—OH), carboxyl groups (—COOH), amino groups (—$NH_2$), imino groups (>NH) or the like on its surface;

preparing a solution by dissolving the chemical adsorbent mentioned above in a nonaqueous organic solvent such as hexane, chloroform, carbon tetrachloride or the like; and dipping and holding the substrate in the prepared solution;

or alternatively, coating the solution on the substrate surface by a spray or roller.

As a result, the chemical adsorbent is covalently bonded to the substrate surface by a dehydrohalogenation or alcohol elimination reaction between the active hydrogens on the substrate surface and the functional groups (halogenosilyl or alkoxysilyl groups) of the chemical adsorbent. After the reaction, the substrate is washed with a nonaqueous organic solution such as chloroform, thus removing unreacted chemical adsorbent. The substrate is then washed with water, and is dried at room temperature or under heat. As a result, a chemically adsorbed ultrathin film (monomolecular film) of a silicon compound comprising 1-pyrrolyl groups is adhered to the substrate surface. The thickness of the monomolecular film can be adjusted by changing the number of carbon atoms contained in the alkyl groups of ω-(1-pyrrolyl)-alkylsilane compound.

Furthermore, a conductive ultrathin film can be formed by the electrolytic or catalytic polymerization of the above-mentioned chemically adsorbed ultrathin film (monomolecular film).

A silicon compound comprising 1-pyrrolyl groups of the invention and method of manufacturing the same are explained by referring to the following examples.

EXAMPLE 1

Prepared 10-(1-pyrrolyl)-1-decene was reacted to trichlorosilane, thus synthesizing 10-(1-pyrrolyl)-decyltrichlorosilane.

The above-noted 10-(1-pyrrolyl)-1-decene was prepared by the following procedure:

placing 8.2 g (0.124 mol) pyrrole and 40 ml tetrahydrofuran in a 500 ml flask, equipped with an agitator, reflux condenser, thermometer and dropping funnel;

dropping 42.6 g (0.100 mol) of 15% butyllithiumhexane solution from the funnel into the flask at 5°–10° C. and reacting the butyllithiumhexane with the pyrrole, thus preparing a solution;

adding 100 ml dimethylsulfoxide to the above-noted solution, and replacing the tetrahydrofuran with the dimethylsulfoxide by heating and distilling the tetrahydrofuran;

dropping 21.9 g (0.100 mol) of 10-bromo-1-decene from the dropping funnel to the solution at 30°–35° C., thus generating a reaction;

adding 100 ml water and 200 ml hexane to the solution after the above-mentioned reaction;

separating an organic layer from the solution and removing dimethylsulfoxide from the layer, thus generating the dissolution of the organic layer; and distilling the organic layer at a 101°–104° C. distillation point and 2 mmHg distillation pressure, thereby providing 13.0 g of purified 10-(1-pyrrolyl)-1-decene.

Then, the above-mentioned 10-(1-pyrrolyl)-decyltrichlorosilane was prepared by the following procedure:

placing 10.2 g (0.050 mol) 10-(1-pyrrolyl)-1-decene and 0.05 g isopropylalcohol solution, containing hydrogenhexachloroplantinate(IV)hydrate ($H_2PtCl_6.6H_2O$) at a concentration of 4%, in a 100 ml flask, equipped with an agitator, reflux condenser, thermometer and dropping funnel, thus preparing a solution;

dropping 8.2 g (0.060 mol) trichlorosilane from the dropping funnel to the solution for one hour at 60°–70° C.; and aging the solution for two hours at 70° C.

The solution was then distilled at a 136°–138° C. distillation point and 1.5 mmHg distillation pressure, thus providing 11.4 g of purified 10-(1-pyrrolyl)-decyltrichlorosilane. The yield was 67.1%.

The results of mass spectrum (MS), nuclear magnetic resonance spectrum (NMR) and infrared absorption spectrum (IR) of the compound, 10-(1-pyrrolyl)-decyltrichlorosilane, are shown below.

Mass Spectrum (MS): m/z (Assignment) 339, 341, 343 (Molecular Ion Peak) 133, 135, 137 (SiCl$_3$)

Nuclear Magnetic Resonance Spectrum (NMR): δ (ppm) (See FIG. 1)

Figure 2:
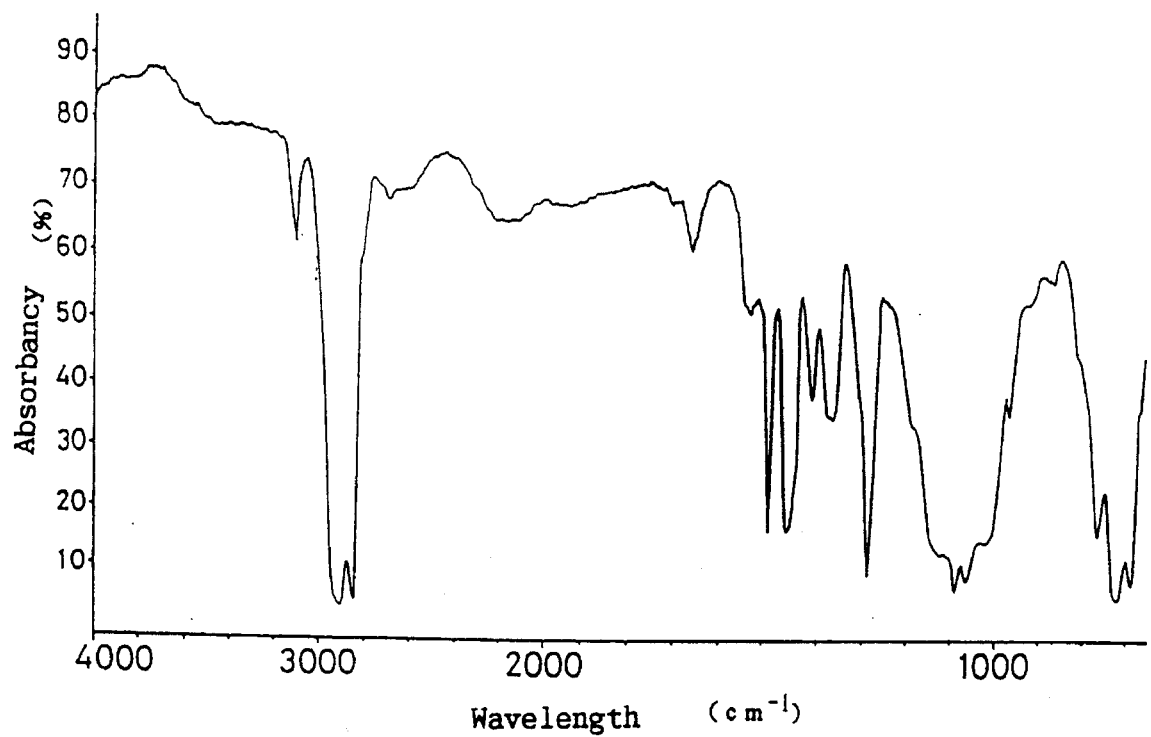
FIG. 2 is a graph showing the infrared absorption spectrum of 10-(1-pyrroyl)-decyltrichlorosilane of Example 1.

Infrared Absorption Spectrum (IR): cm$^{-1}$ (See FIG. 2)

According to the results, the compound was proved to be 10-(1-pyrrolyl)decyltrichlorosilane.

EXAMPLE 2

A chemically adsorbed ultrathin film formed by using the silicon compound comprising 1-pyrrolyl groups and a method of manufacturing the same are explained below by referring to FIG. 3.

Figure 3:
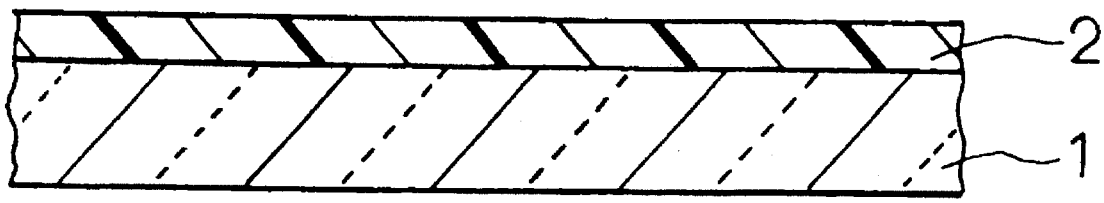
FIG. 3 is a schematic illustration of a chemically adsorbed ultrathin film (monomolecular film) of Example 2.

The method of manufacturing the ultrathin film is as follows:

dissolving 10 mg silicon compound comprising 1-pyrrolyl groups, such as 10-(1-pyrrolyl)-decyltrichlorosilane, in a 100 ml mixed solvent of 80% by weight of n-hexadecane (toluene, xylene, hexane or the like), 12% by weight of carbon tetrachloride and 8% by weight of chloroform, thus preparing a solution;

washing a substrate such as a quartz substrate 1 of FIG. 3 (or metallic plate, quartz plate, ceramic substrate, molded plastic substrate, etc.) with an organic solvent or water;

drying the substrate;

dipping and holding the substrate in the prepared solution for one hour (wherein the time for dipping and holding the substrate varies depending on the type of substrate and the surface roughness of the substrates);

reacting the hydroxyl groups on the substrate surface to the SiCl groups of the 10-(1-pyrrolyl)-decyltrichlorosilane, thereby generating a dehydrochlorination reaction as shown in Formula 15;

Formula 15

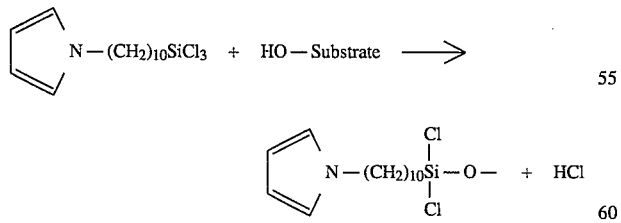

washing and removing unreacted 10- (1-pyrrolyl)-decyltrichlorosilane with a nonaqueous solvent such as Freon-113;

reacting the substrate with water, thus hydrolyzing the chlorosilyl groups to become silanol groups as shown in Formula 16; and Formula 16

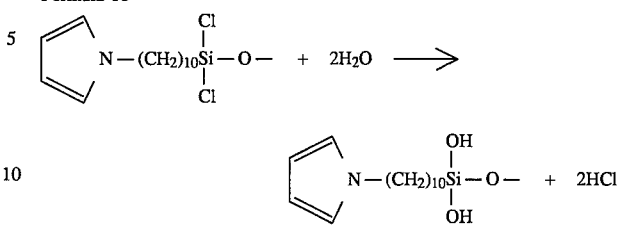

drying the substrate, thereby dehydrating and crosslinking the silanol groups and forming siloxane bonds and a chemically adsorbed ultrathin film (monomolecular film) as shown in Formula 17.

Formula 17

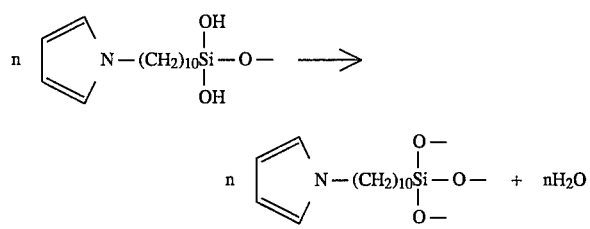

By following the above-noted procedures, a chemically adsorbed ultrathin film (monomolecular film) 2 comprised of 10-(1 -pyrrolyl)-decylsilanol was chemically bonded to the surface of substrate 1. The thickness of the film was about 2.5 nm (FIG. 3).

Moreover, a quartz substrate formed with chemically adsorbed ultrathin film (monomolecular film) 2 was dipped and held in 300 ml ether solution, containing ferric chloride anhydride at a concentration of 0.12 mol/l. The formation of the monomolecular film was confirmed by analysis with a Fourier transform infrared absorption spectrochemical instrument.

EXAMPLE 3

Figure 4:
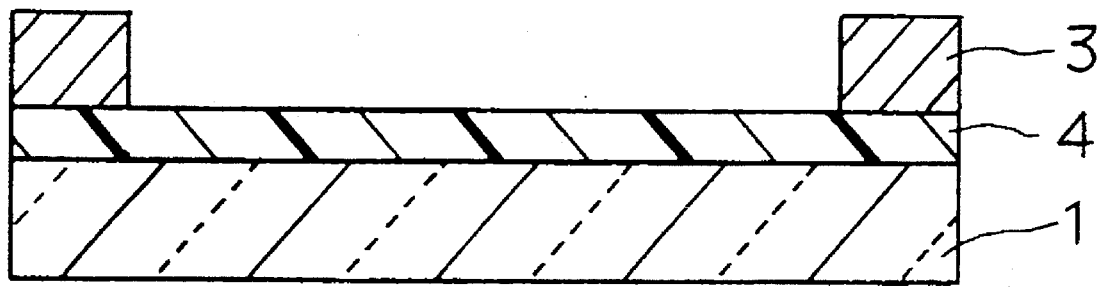
FIG. 4 is a schematic illustration of a polypyrrole derivative ultrathin film of Example 3.

A polypyrrole derivative ultrathin film, formed by polymerizing the above-mentioned ultrathin film, and method of manufacturing the same are explained by referring to FIG. 4.

A polypyrrole derivative ultrathin film 4 was formed on a substrate surface in the following procedures:

depositing platinum 3 to a section of the ultrathin film surface, thus preparing a working electrode;

preparing an acetonitrile solution, containing lithium perchlorate anhydride (tetraethylammoniumtetrafluoroborate, tetrabutylammoniumperchlorate or the like) at a concentration of 0.05 mol/l, as a supporting electrolyte;

dipping and holding substrate 1 formed with the chemically adsorbed ultrathin film, along with a gold counter electrode and a NaCl-calomel reference electrode, in the prepared solution; and polymerizing the substrate with 100 V per second scanning speed and 150 μA/cm$^2$ current density in an inert gas (such as helium gas) atmosphere.

The formation of polypyrrole derivative ultrathin film 4 was proved by analysis with a Fourier transform infrared absorption spectrochemical instrument.

As explained above, in applying a silicon compound comprising 1-pyrrolyl groups of the invention and method of manufacturing the same, a pyrrolyl derivative ultrathin film can be formed firmly on a substrate surface. The conductive ultrathin film, moreover, can be easily formed by the electrolytic or catalytic polymerization of the chemically adsorbed ultrathin film (monomolecular film).

The invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. A chemical compound comprising 1-pyrrolyl groups and silicon groups as represented by Formula C:

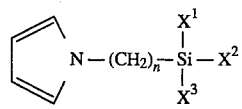

Formula C wherein $X^1$, $X^2$ and $X^3$ are the same or different and represent a halogen atom or an alkoxy group with 1–4 carbon atoms and n represents an integer from 8 to 30.

2. The chemical compound according to claim 1, wherein at least one of $X^1$, $X^2$ and $X^3$ is a halogen atom.

3. The chemical compound according to claim 1, wherein at least two of $X^1$, $X^2$ and $X^3$ are a halogen atom.

4. The chemical compound according to claim 1, wherein $X^1$, $X^2$ and $X^3$ are a halogen atom.

* * * * *